US012575819B2

(12) United States Patent
Hartson et al.

(10) Patent No.: US 12,575,819 B2
(45) Date of Patent: Mar. 17, 2026

(54) SOFT TISSUE IMPLANT SYSTEMS, INSTRUMENTS, AND RELATED METHODS

(71) Applicant: Paragon 28, Inc., Englewood, CO (US)

(72) Inventors: Kyle Hartson, Denver, CO (US); Paul Devasconcellos, Parker, CO (US)

(73) Assignee: Paragon 28, Inc., Englewood, CO (US)

( * ) Notice: Subject to any disclaimer, the term of this patent is extended or adjusted under 35 U.S.C. 154(b) by 497 days.

(21) Appl. No.: 18/061,693

(22) Filed: Dec. 5, 2022

(65) Prior Publication Data

US 2023/0115148 A1     Apr. 13, 2023

Related U.S. Application Data

(63) Continuation of application No. PCT/US2021/034769, filed on May 28, 2021.

(60) Provisional application No. 63/034,066, filed on Jun. 3, 2020.

(51) Int. Cl.
*A61B 17/04*          (2006.01)

(52) U.S. Cl.
CPC .. *A61B 17/0401* (2013.01); *A61B 2017/0409* (2013.01); *A61B 2017/0464* (2013.01)

(58) Field of Classification Search
CPC ........ A61B 17/0401; A61B 2017/0409; A61B 2017/0464; A61F 2/1662; A61F 2/1664
See application file for complete search history.

(56) References Cited

U.S. PATENT DOCUMENTS

| | | | |
|---|---|---|---|
| 8,696,716 B2 | 4/2014 | Kartalian |
| 2008/0177302 A1 | 7/2008 | Shurnas |
| 2012/0109156 A1 | 5/2012 | Overes |

| | | | |
|---|---|---|---|
| 2016/0113757 A1 | 4/2016 | Diduch |
| 2016/0128682 A1 | 5/2016 | Konrath et al. |
| 2017/0128061 A1 | 5/2017 | Stone |
| 2017/0265988 A1 | 9/2017 | Sengun |

(Continued)

FOREIGN PATENT DOCUMENTS

| | | |
|---|---|---|
| JP | 2011528270 | 11/2011 |

OTHER PUBLICATIONS

Extended European Search Report, European Patent Application No. EP21818464.6, dated Apr. 30, 2024, 8 pages.

(Continued)

*Primary Examiner* — Ashley L Fishback

(74) *Attorney, Agent, or Firm* — Heslin Rothenberg Farley & Mesiti P.C.

(57)          ABSTRACT

The present disclosure relates to instruments, implant systems, and methods for joining bone and/or tissue portions. The instrument includes a handle portion; an inserter portion comprising an insertion portion and a tip portion; a guide portion comprising a medial end component and a distal end component, the guide portion extending from a distal end portion of the handle portion to a bone engagement end of the inserter portion; a passageway extending through the inserter portion from the distal end of the handle portion to the bone engagement end of the inserter portion; and a hole that extends from an exterior surface of the handle portion and the guide portion to the passageway, wherein the insertion portion and the tip portion of the inserter portion are positioned past the distal end component of the guide portion when the handle portion, the inserter portion, and the guide portion are mated.

20 Claims, 17 Drawing Sheets

(56)                    References Cited

U.S. PATENT DOCUMENTS

2018/0221013  A1     8/2018   Marks et al.

OTHER PUBLICATIONS

International Preliminary Report on Patentability for International
Application No. PCT/US2021/034769 dated Dec. 6, 2022, 8 pages,
International Bureau of WIPO.
International Search Report and Written Opinion of the Interna-
tional Searching Authority for PCT/US2021/034769, Aug. 25, 2021,
10 pages.

SOFT TISSUE IMPLANT SYSTEMS, INSTRUMENTS, AND RELATED METHODS

CROSS REFERENCE TO RELATED APPLICATION

This application is a by-pass continuation of PCT International Application No. PCT/US2021/034769, filed May 28, 2021, and entitled "Soft Tissue Implant systems, Instruments, and Related Methods," which claims priority benefit under 35 U.S.C. § 119(e) of U.S. Provisional Patent Application No. 63/034,066, filed Jun. 3, 2020, and entitled "Soft Tissue Implant systems, Instruments, and Related Methods," which are incorporated herein by reference in their entireties.

FIELD

The present disclosure relates to soft tissue implant systems, instruments, and related methods. The present disclosure relates to podiatric and orthopedic implants and surgery related to repairs of soft tissue and/or bone. More specifically, but not exclusively, the present disclosure relates to instruments, implants, systems, assemblies, and methods for joining soft tissue to soft tissue, soft tissue to bone, and bone to bone.

BACKGROUND

The plantar plate is a thick ligamentous (fibrocartilaginous) structure on the bottom of the foot under a metatarsophalangeal joint (MTP joint). A plantar plate attaches to a metatarsal bone and a corresponding proximal phalanx bone. A plantar plate provides stability to the MTP joint by withstanding compressive loads from the metatarsal head and tensile loads in line with the toe axis. A plantar plate also cushions the bottom of an MTP joint and the distal head of a metatarsal while standing, walking, running, and the like. A plantar plate also helps bring the corresponding toe toward the floor while standing.

A plantar plate may become torn or otherwise compromised, such as due to biomechanical abnormalities and/or imbalances in the foot that cause overload of one of the metatarsals and/or MTP joints. Examples of biomechanical abnormalities and/or imbalances include a long first metatarsal, a short second metatarsal, a short third metatarsal, an untreated metatarsus adductus deformity (e.g., a pigeon toe deformity), arthritis of the great toe (first metatarsal, first proximal phalanx and/or first distal phalanx), and prior cortisone injection into a plantar plate.

The tissue of the plantar plate itself may become attenuated, tear or otherwise become segmented along its length between corresponding metatarsal and proximal phalanx bones. Alternatively, a plantar plate may tear from or otherwise become decoupled from corresponding metatarsal or proximal phalanx bones. A torn plantar plate typically causes persistent ball of the foot pain and/or changes in the position/alignment of the affected toe and/or adjacent toe(s) (e.g., hammertoe). Both acute and, more commonly, chronic injuries to the plantar plate can cause a range of injury types, such as instability (particularly in the 2nd and 3rd MTP joints, medial deviation of the toe, "crossover toe", pain and discomfort, for example).

Other tissues and/or bones of the foot, and other parts of a mammalian (e.g., human) body, similarly may become torn or otherwise be segmented or separated such that joining of the portions of the tissues and/or bones may be anatomically and/or physiologically advantageous or desirable. For example, the human hand includes a palmar plate. The palmar plate is an analogous structure to the plantar plate. A palmar plate is associated with each metacarpophalangeal joint (MCP joint) and each interphalangeal joint in the hand. Like the plantar plate, the palmar plate may tear.

Typical plantar plate repair options include suturing/re-approximating the tear in the plantar plate tissue to induce healing, or re-attaching the tissue to the insertion point at the base of the proximal phalanx. Current systems for plantar plate repair (and repairs of other tissues and/or bones of the foot, and other parts of the human body) tend to be bulky and/or complex. Current systems also typically require multiple and/or relatively large through holes to be formed per tissue and/or bone connection in order to join/repair the portions, which can weaken the construct.

All-suture soft anchor implants generally rely on bone quality and consistency for deployment. When tension is applied to anchors of an implant, those anchors deform within the cancellous bone space and deploy against the cortical bone to provide secure anchoring. In cases where bone quality or consistency is not optimal, these anchors may fail to deploy. Products can have up to about a ten percent non-deployment rate.

Thus, there is a need for instruments, implants, systems, assemblies, and methods for plantar plate repair, and joining of other tissues and/or bones of the foot and other parts of a mammalian (e.g., human) body, that are compact, maneuverable and simple to use. There is also need for tissue and/or bone repair/joining instruments for deployment of implants, systems, assemblies, and methods that do not require a plurality of and/or relatively large through holes formed in each of the joined tissue and/or bone segments.

The present disclosure is directed to overcoming these and other deficiencies in the art.

SUMMARY

A first aspect relates to an instrument. The instrument includes a handle portion; an inserter portion comprising an insertion portion and a tip portion; a guide portion comprising a medial end component and a distal end component, the guide portion extending from a distal end portion of the handle portion to a bone engagement end of the inserter portion; a passageway extending through the inserter portion from the distal end of the handle portion to the bone engagement end of the inserter portion; and a hole that extends from the exterior surface of the handle portion and the guide portion to the passageway, wherein the guide portion is configured such that the insertion portion and the tip portion of the inserter portion are positioned past the distal end component of the guide portion when the handle portion, the inserter portion, and the guide portion are mated.

In one embodiment, the guide portion further comprises a guide handle. In another embodiment, the handle portion comprises a first coupling portion. In another embodiment, the handle portion comprises a second coupling portion. In one embodiment, the instrument further includes an end cap portion.

In one embodiment, the instrument further includes a cavity extending from a proximal end of the handle portion to the distal end of the handle portion. In another embodiment, the distal end of the second coupling portion of the handle portion comprises an opening. In one embodiment, the tip portion comprises at least one tooth. In one embodiment, the tip portion comprises a forked free end. In another embodiment, the tip portion comprises a pair of tines and a base portion extending therebetween. In another embodiment, the tip portion comprises a pair of grooves extending proximally from the base portion of a forked free end. In one embodiment, the tip portion is configured to retain an anchor tube of an implant thereon.

In one embodiment, the instrument further includes an implant system, wherein a first flexible anchor tube or a second flexible anchor tube of the implant system is retained on the tip portion. In another embodiment, one or more end portions of a first flexible anchor tube or a second flexible anchor tube retained on the tip portion extends within the pair of grooves of the tip portion, and a medial portion thereof extends over a base portion between a pair of tines.

A second aspect relates to a bone and/or tissue joining implant system. The system includes an instrument comprising a handle portion; an inserter portion comprising an insertion portion and a tip portion; a guide portion comprising a medial end component and a distal end component, the guide portion extending from a distal end portion of the handle portion to a bone engagement end of the inserter portion; a passageway extending through the inserter portion from the distal end of the handle portion to the bone engagement end of the inserter portion; and a hole that extends from the exterior surface of the handle portion and the guide portion to the passageway, wherein the guide portion is configured such that the insertion portion and the tip portion of the inserter portion are positioned past the distal end component of the guide portion when the handle portion, the inserter portion, and the guide portion are mated, and one or more sutures.

In one embodiment, the guide portion further comprises a guide handle. In another embodiment, the handle portion comprises a first coupling portion. In another embodiment, the handle portion comprises a second coupling portion. In one embodiment, the bone and/or tissue joining implant system further includes an end cap portion.

In one embodiment, the bone and/or tissue joining implant system further includes a cavity extending from a proximal end of the handle portion to the distal end of the handle portion. In another embodiment, the distal end of the second coupling portion of the handle portion comprises an opening. In one embodiment, the tip portion comprises at least one tooth. In another embodiment, the tip portion comprises a forked free end. In one embodiment, the tip portion comprises a pair of tines and a base portion extending therebetween. In another embodiment, the tip portion comprises a pair of grooves extending proximally from the base portion of a forked free end. In yet another embodiment, the tip portion is configured to retain an anchor tube of an implant thereon.

In one embodiment, the bone and/or tissue joining implant system further includes a first flexible anchor tube or a second flexible anchor tube of the implant system that is retained on the tip portion. In another embodiment, one or more end portions of a first flexible anchor tube or a second flexible anchor tube retained on the tip portion extends within the pair of grooves of the tip portion, and a medial portion thereof extends over a base portion between a pair of tines.

A third aspect relates to a method of using an instrument to deploy a bone and/or tissue joining implant system. The method includes providing an instrument, the instrument comprising a handle portion; an inserter portion comprising an insertion portion and a tip portion; a guide portion comprising a medial end component and a distal end component, the guide portion extending from a distal end portion of the handle portion to a bone engagement end of the inserter portion; a passageway extending through the inserter portion from the distal end of the handle portion to the bone engagement end of the inserter portion; and a hole that extends from the exterior surface of the handle portion and the guide portion to the passageway, wherein the guide portion is configured such that the insertion portion and the tip portion of the inserter portion are positioned past the distal end component of the guide portion when the handle portion, the inserter portion, and the guide portion are mated. The method further includes passing a first anchor tube through at least a portion of a first bone or tissue segment; passing a first end portion of at least one suture through a first portion of a second bone or tissue segment; and passing a second end portion of at least one suture through a second portion of a second bone or tissue segment.

In one embodiment, the method further includes tensioning the first and second end portions of the at least one suture in divergent directions to seat the first anchor tube against the first bone or tissue segment, deform the first anchor tube, and drawing the first bone or tissue segment and the second bone or tissue segment together. In a further embodiment, the method further includes tying the first and second end portions of the at least one suture in a knot to fix the relationship of the first bone or tissue segment and the second bone or tissue segment. In yet another embodiment, passing the first anchor tube through at least a portion of the first bone or tissue segment comprises passing the first anchor tube partially through a first bone segment past a cortex thereof.

In one embodiment, passing the first end portion of the at least one suture through the first portion of the second bone or tissue segment comprises passing an instrument coupled to the first end portion of the at least one suture through the first portion of the second bone or tissue segment; and passing the second end portion of the at least one suture through the second portion of the second bone or tissue segment comprises passing an instrument coupled to the second end portion of the at least one suture through the second portion of the second bone or tissue segment.

In one embodiment, passing the first end portion of the at least one suture through the first portion of the second bone or tissue segment comprises first passing the first end portion of the at least one suture through the first portion of the second bone or tissue segment from a first surface of the second bone or tissue segment that is adjacent to the first bone or tissue segment to a second surface of the second bone or tissue segment that is distal to the first bone or tissue segment, and passing the second end portion of the at least one suture through the second portion of the second bone or tissue segment comprises first passing the second end portion of the at least one suture through the second portion of the second bone or tissue segment from the first surface to the second surface of the second bone or tissue segment.

In one embodiment, the first bone or tissue segment comprises a proximal phalanx and the second bone or tissue segment comprises a plantar plate. In another embodiment, the guide portion further comprises a guide handle. In another embodiment, the handle portion comprises a first coupling portion. In yet another embodiment, the handle portion comprises a second coupling portion. In one embodiment, the method further includes an end cap portion. In another embodiment, the method further includes a cavity extending from a proximal end of the handle portion to the distal end of the handle portion. In one embodiment, the distal end of the second coupling portion of the handle portion comprises an opening.

In one embodiment, the tip portion comprises at least one tooth. In another embodiment, the tip portion comprises a forked free end. In another embodiment, the tip portion comprises a pair of tines and a base portion extending therebetween. In yet another embodiment, the tip portion comprises a pair of grooves extending proximally from the base portion of a forked free end. In one embodiment, the tip portion is configured to retain an anchor tube of an implant thereon. In one embodiment, the method further includes an implant system, wherein a first flexible anchor tube or a second flexible anchor tube of the implant system is retained on the tip portion. In one embodiment, the one or more end portions of a first flexible anchor tube or a second flexible anchor tube retained on the tip portion extends within the pair of grooves of the tip portion.

The present disclosure is directed toward devices and methods for joining tissue and/or bone segments or portions. The instruments, implants, systems, assemblies, and methods for joining soft tissue to soft tissue, soft tissue to bone, and bone to bone may be used for repairing a torn plantar plate. However, the instruments, implants, systems, assemblies, and methods may be equally employed to repair/join any other tissue and/or bone segments or portions of the foot or other parts of the mammalian (e.g., human) body.

The present disclosure relates to deploying soft anchors using accessory instrumentation or features that do not rely solely on native bone for use. In particular, the present disclosure relates to a feature for an inserter to aid in deployment of an implant. The feature may, for example, be a thin-walled sleeve that is designed to be inserted into a prepared bone hole behind an anchor and kept in place while an insertion fork is removed. In this way, the anchor deploys against the sleeve rather than relying on the cortical wall for anchor deployment. The present disclosure allows for the operator to have tactile confirmation of anchor deployment and does not depend solely on native bone quality and consistency for deployment.

These and other objects, features, and advantages of the aspects disclosed herein will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION

Figure 1:
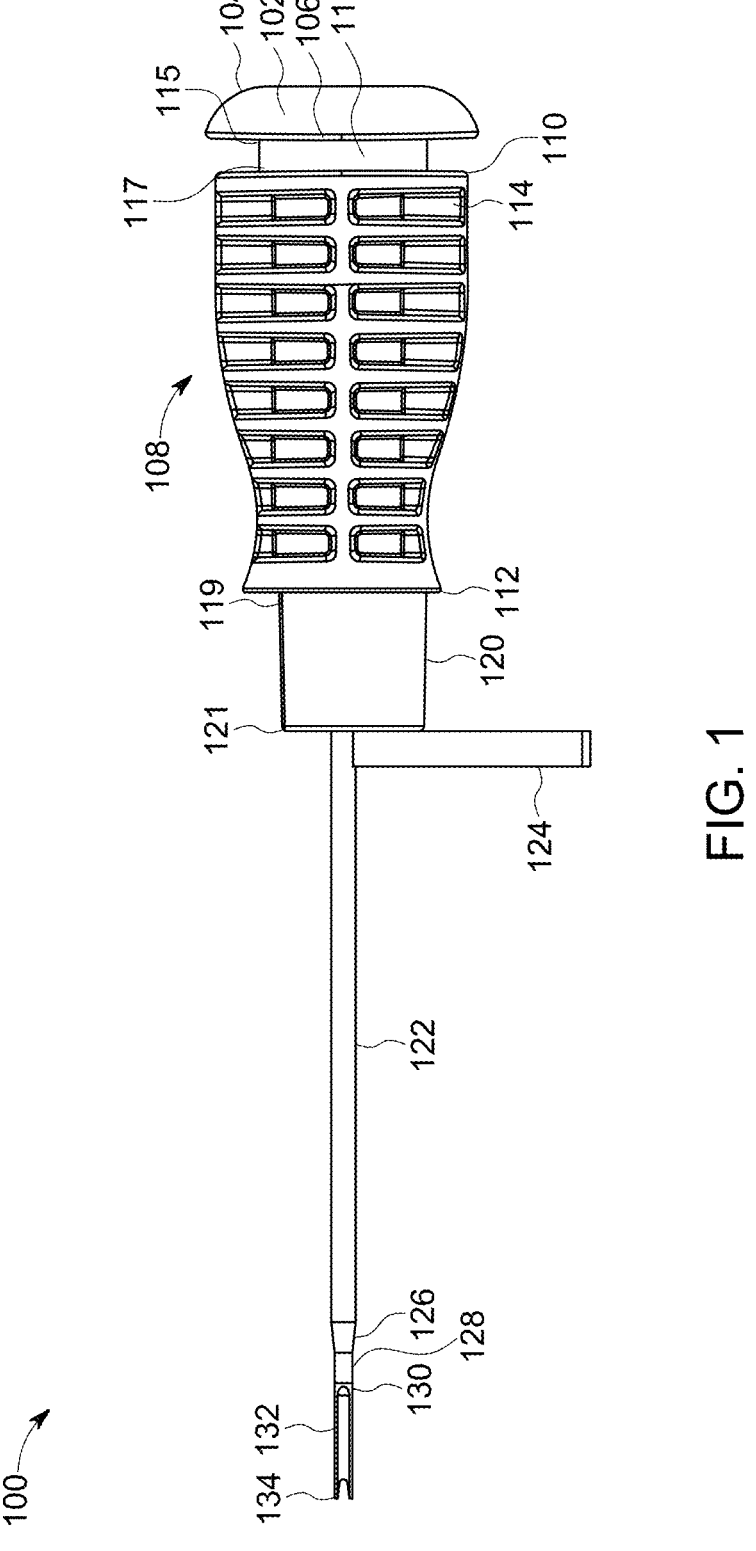
FIG. 1 is a side view of an exemplary drill guide and inserter system for facilitating implantation of an implant system, in accordance with the present disclosure.
Figure 2:
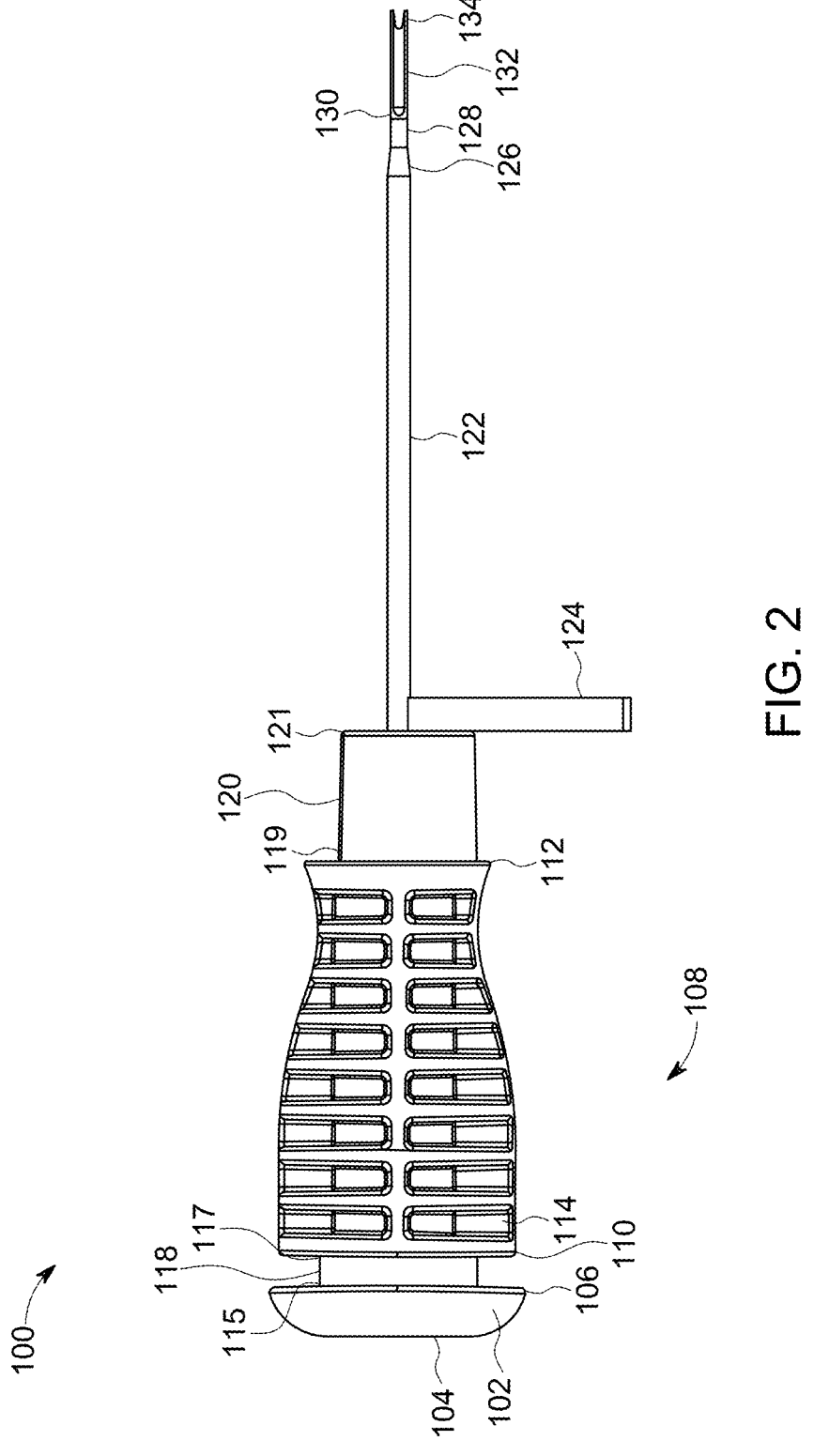
FIG. 2 is a side view of an exemplary drill guide and inserter system for facilitating implantation of an implant system, in accordance with the present disclosure.
Figure 3:
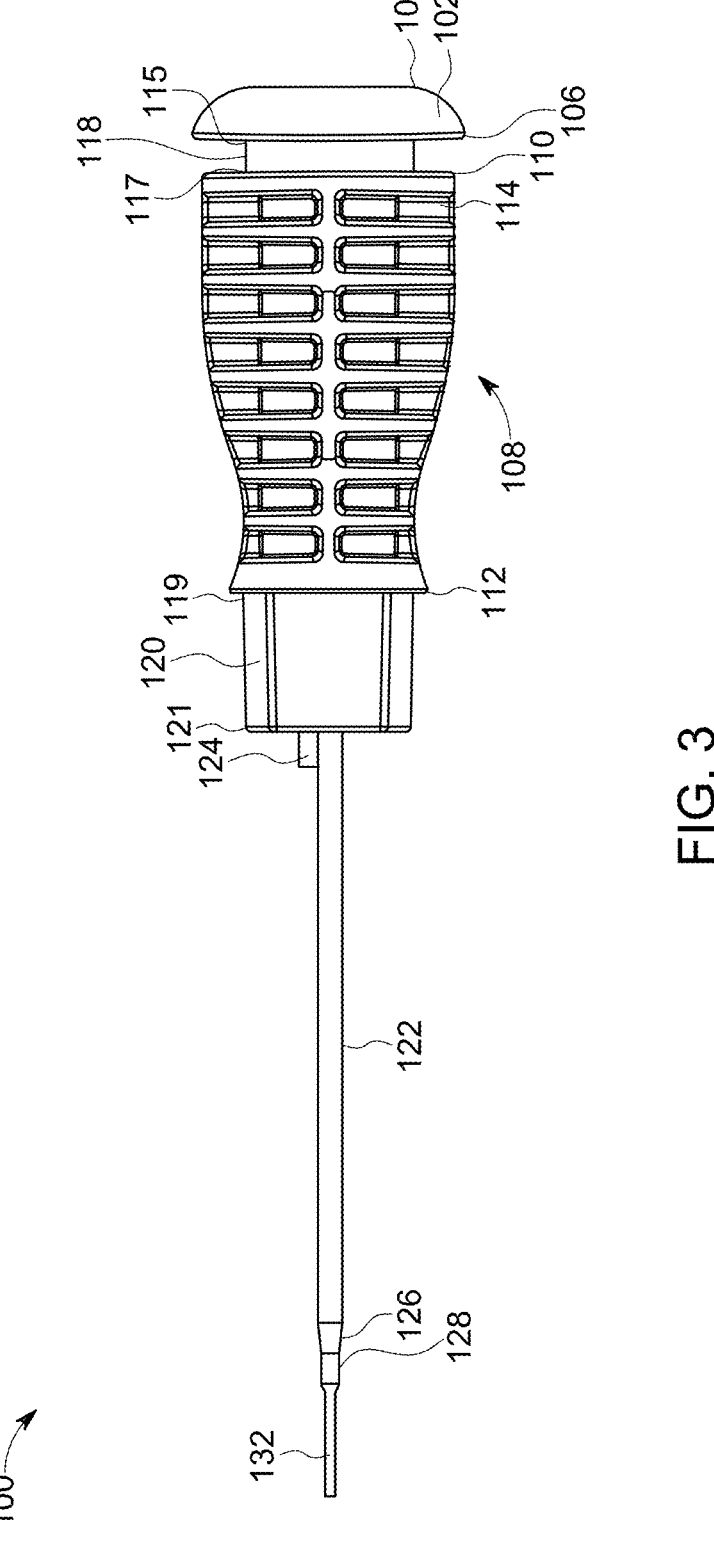
FIG. 3 is a top perspective view of an exemplary drill guide and inserter system for facilitating implantation of an implant system, in accordance with the present disclosure.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers to the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

Generally stated, disclosed herein are instruments, implants, systems, assemblies, and methods for joining soft tissue to soft tissue, soft tissue to bone, and bone to bone. The implants, systems, assemblies and methods may be used for repairing a torn plantar plate of a metatarsophalangeal joint (MTP joint). While the instruments, implants, systems, assemblies, and methods may be illustrated and described in the present disclosure in the context of plantar plate repair, the instruments, implants, systems, assemblies, and methods may equally be employed or may be adapted without undue experimentation to join any soft tissue to any soft tissue, any soft tissue to any bone, or any bone to any bone. For example, the instruments, implants, systems, assemblies, and methods may be equally employed to repair/join any other tissue and/or bone segments or portions of the foot or other parts of the mammalian (e.g., human) body, such as but not limited to a torn palmar plate.

The instruments, implants, systems, assemblies, and related methods for joining soft tissue to soft tissue, soft tissue to bone, and bone to bone of the present disclosure may be similar to, such as include at least one feature or aspect of, the implants, systems, assemblies and related methods disclosed in U.S. Provisional Patent Application No. 62/968,765, filed on Jan. 31, 2020, and entitled Knotless Soft Tissue Implant Systems and Related Methods; U.S. Provisional Patent Application No. 62/775,591, filed on Dec. 5, 2018, and entitled Implant System and Methods of Use; U.S. Provisional Patent Application No. 62/883,429, filed on Aug. 6, 2019, and entitled Soft Tissue Implant Systems, Instruments and Related Method; and/or International PCT Application No. PCT/US2019/064741, filed on Dec. 5, 2019, and entitled Soft Tissue Implant Systems, Instruments and Related Methods, which are hereby incorporated herein by reference in their entireties. Similarly, the instruments, implants, systems, assemblies, and related methods for joining soft tissue to soft tissue, soft tissue to bone, and bone to bone of the present disclosure may include one or more instrument (e.g., one or more insertion and/or implantation instruments) disclosed in U.S. Provisional Patent Application No. 62/968,765, filed on Jan. 31, 2020, and entitled Knotless Soft Tissue Implant Systems and Related Methods; U.S. Provisional Patent Application No. 62/883,429, filed on Aug. 6, 2019, and entitled Soft Tissue Implant Systems, Instruments and Related Method; and/or International PCT Application No. PCT/US2019/064741, filed on Dec. 5, 2019, and entitled Soft Tissue Implant Systems, Instruments and Related Methods, which are incorporated herein by reference in their entireties.

Referring to the drawings, wherein like reference numerals are used to indicate like or analogous components throughout the several views, and with particular reference to FIGS. 1-17, there is illustrated an exemplary embodiment of a drill guide and inserter system 100 for joining soft tissue to soft tissue, soft tissue to bone, or bone to bone according to the present disclosure.

FIGS. 1-17 illustrate an exemplary drill guide and inserter system, instrument, device or apparatus 100 for facilitating implantation of an implant system in accordance with the present disclosure. The drill guide and inserter system 100 is configured to create one or more through holes in one or more bones or tissues and to implant an implant system into/through the one or more through holes in the one or more bones or tissues.

As shown in FIGS. 1-4 and 9-14, the drill guide and inserter system 100 includes a handle portion or component 108, an inserter portion or component 138 (see, e.g., FIGS. 9-13), and a guide portion or component 122 that are configured to nest or otherwise couple together. As shown in FIGS. 1-4, the handle portion 108 is manually engageable and includes a first coupling portion 118 of the handle portion 108 and a second coupling portion 120 of the handle portion 108. The handle portion 108 may further be proximate to inserter portion 138 or a component that extends from or past a distal end 112 of the handle portion 108 (e.g., the second coupling portion) and defines a bone engagement free end 130.

As shown in FIGS. 1-4, the handle portion 108 of the drill guide and inserter system 100 comprises both a proximal end 110 of the handle portion 108 and a distal end 112 of the handle portion 108. The handle portion 108 is configured to allow a user to securely grasp the handle portion 108 using one hand and position the guide portion 122 and bone engagement free end 130 of the insertion portion 132 and/or inserter portion 138 against a bone (e.g., a plantar side of a proximal phalanx). In one embodiment, the handle portion may include a distal projection to further allow for a user to securely grasp the handle portion 108 using one hand and position the guide portion 122 and the free end of the insertion portion 132 and/or inserter portion 138 against a bone (e.g., a plantar side of a proximal phalanx). The handle portion 108 is also configured to allow the user to secure the guide portion 122 and tip portion 134 of the inserter portion 138 against a bone via one hand (e.g., a plantar side of a proximal phalanx) by applying pressure to the drill guide and inserter system 100 via the user's thumb against the proximal side of the handle, and potentially wrapping one or more fingers of the user's hand around the opposing side of the bone (e.g., the dorsal aspect of the patient's foot) to provide back pressure.

As further shown in FIGS. 1, 2, 9, and 10, for example, the tip portion 134 of the insertion portion 132 of inserter portion 138 may provide at least one relatively sharp point, tip or tooth that may securely engage bone to provide stability of the placement of the drill guide and inserter system 100 and the inserter portion 138 against the bone while the guide portion 122 surrounds the inserter portion 138, while in use. For example, in one embodiment, the tip portion 134 of the insertion portion 132 comprises a plurality of angularly or circumferentially spaced teeth configured to engage bone, as shown in FIGS. 1, 2, 9 and 10.

The handle portion 108 may include on the proximal end 110 of the handle portion 108 a first coupling portion 118. The first coupling portion 118 may include a distal end 117 which may be adjacent to the proximal end of 112 of the handle and may further include a proximal end 115 which may be adjacent to an end cap portion 102. The handle portion 108 may further include on the distal end 112 of the handle portion 108 a second coupling portion 120. The second coupling portion 120 may include a distal end 121 which may be adjacent to the inserter portion 138 and may further include a proximal end 119 which may be adjacent to the distal end 110 of the handle portion 108.

Figure 4:
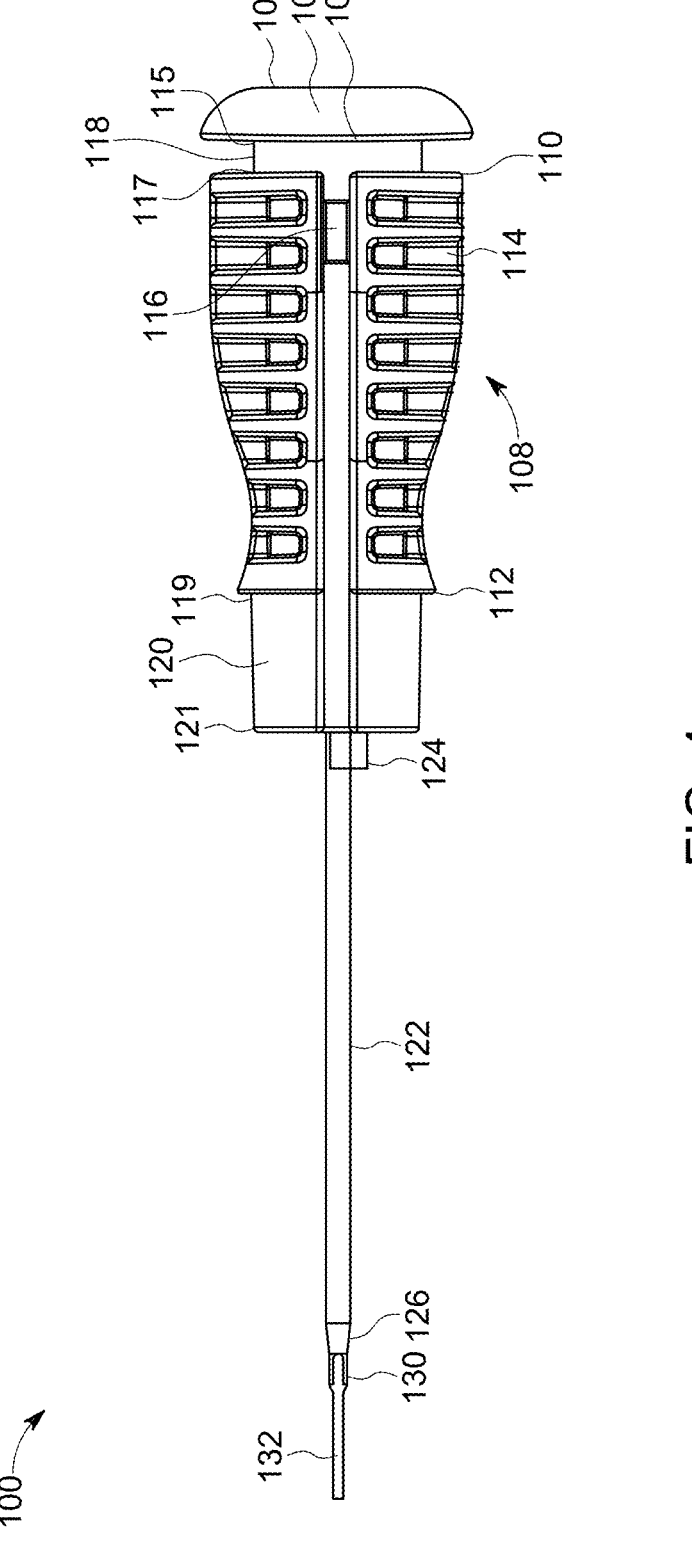
FIG. 4 is a bottom perspective view of an exemplary drill guide and inserter system for facilitating implantation of an implant system, in accordance with the present disclosure.
Figure 5:
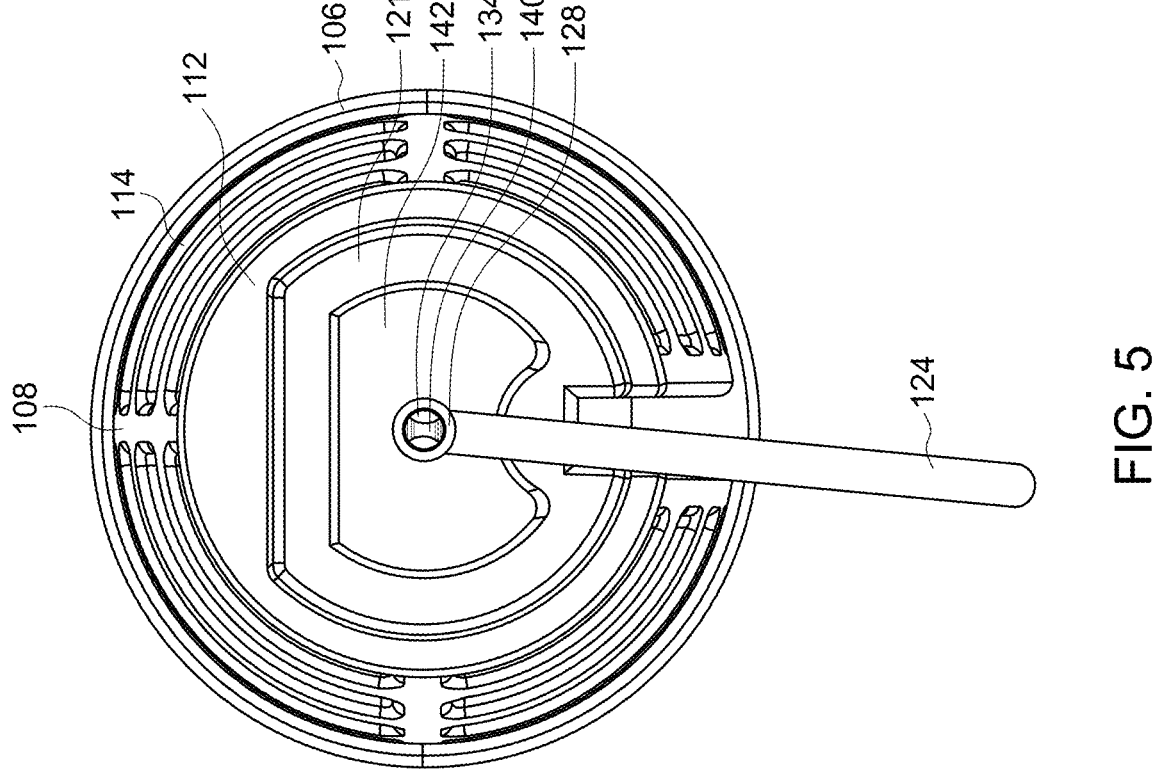
FIG. 5 is a front view of an exemplary drill guide and inserter system for facilitating implantation of an implant system, in accordance with the present disclosure.
Figure 6:
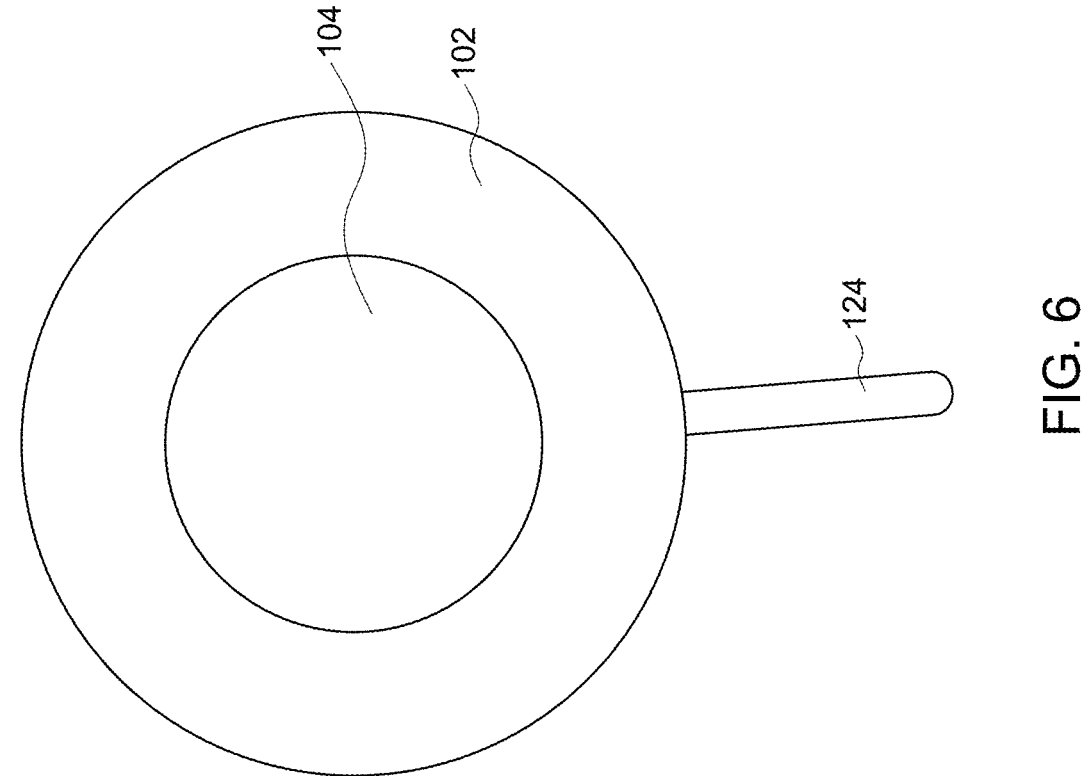
FIG. 6 is a rear view of an exemplary drill guide and inserter system for facilitating implantation of an implant system, in accordance with the present disclosure.
Figure 7:
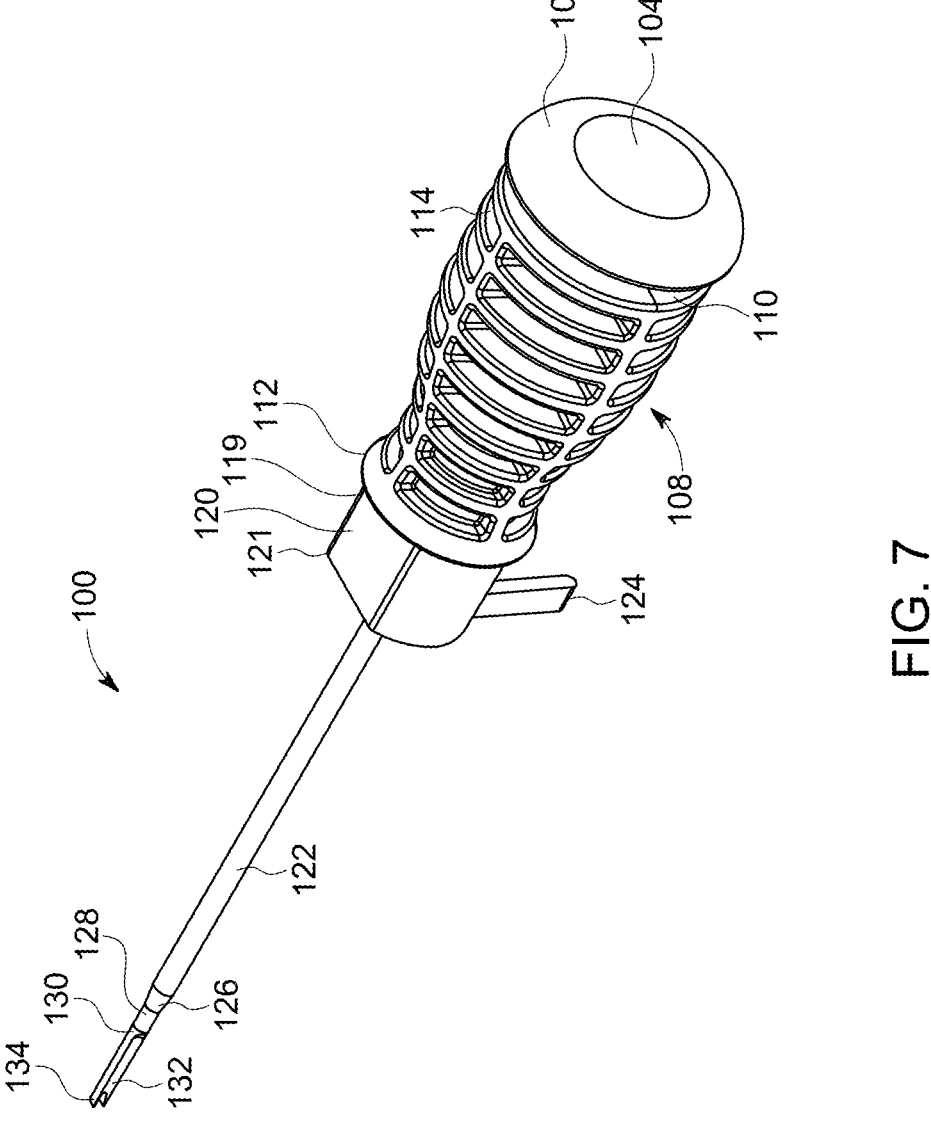
FIG. 7 is a back elevational, perspective view of an exemplary drill guide and inserter system for facilitating implantation of an implant system, in accordance with the present disclosure.
Figure 8:
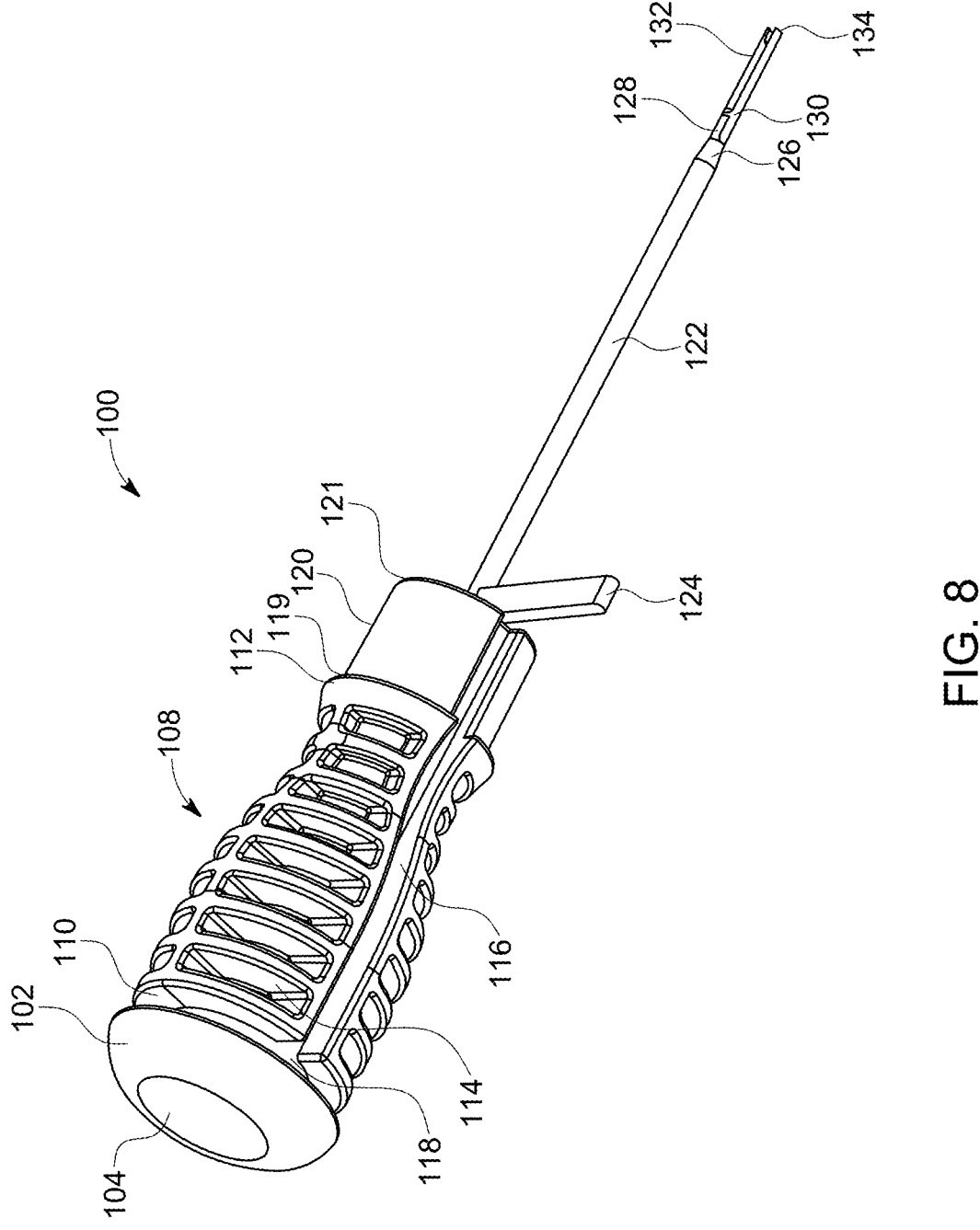
FIG. 8 is a back elevational, perspective view of an exemplary drill guide and inserter system for facilitating implantation of an implant system, in accordance with the present disclosure.
Figure 9:
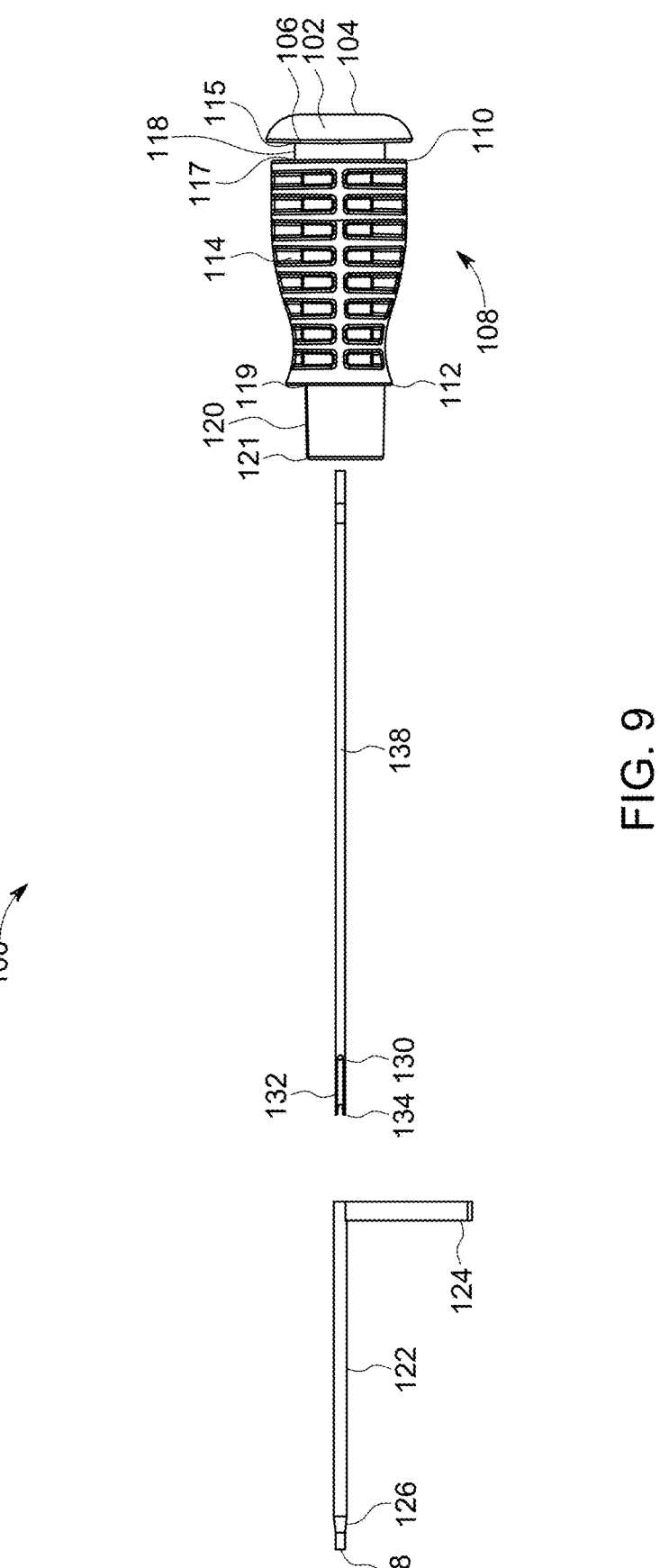
FIG. 9 is an exploded side view of an exemplary drill guide and inserter system for facilitating implantation of an implant system, in accordance with the present disclosure.
Figure 10:
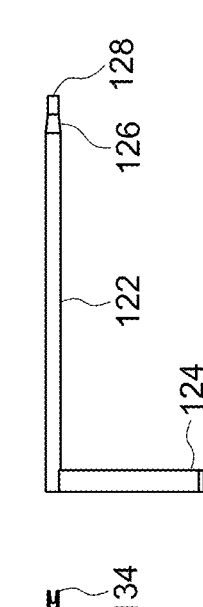
FIG. 10 is an exploded side view of an exemplary drill guide and inserter system for facilitating implantation of an implant system, in accordance with the present disclosure.
Figure 10:
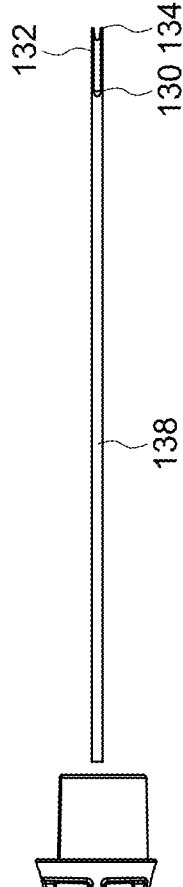
Figure 10:
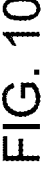
Figure 11:
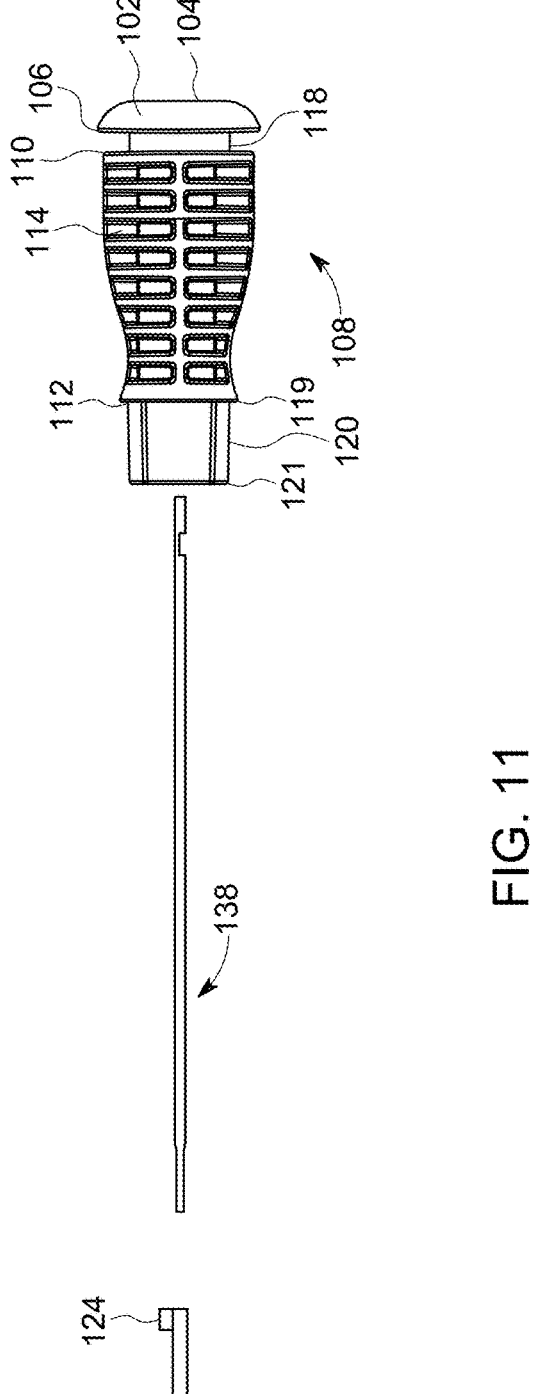
FIG. 11 is an exploded top view of an exemplary drill guide and inserter system for facilitating implantation of an implant system, in accordance with the present disclosure.
Figure 12:
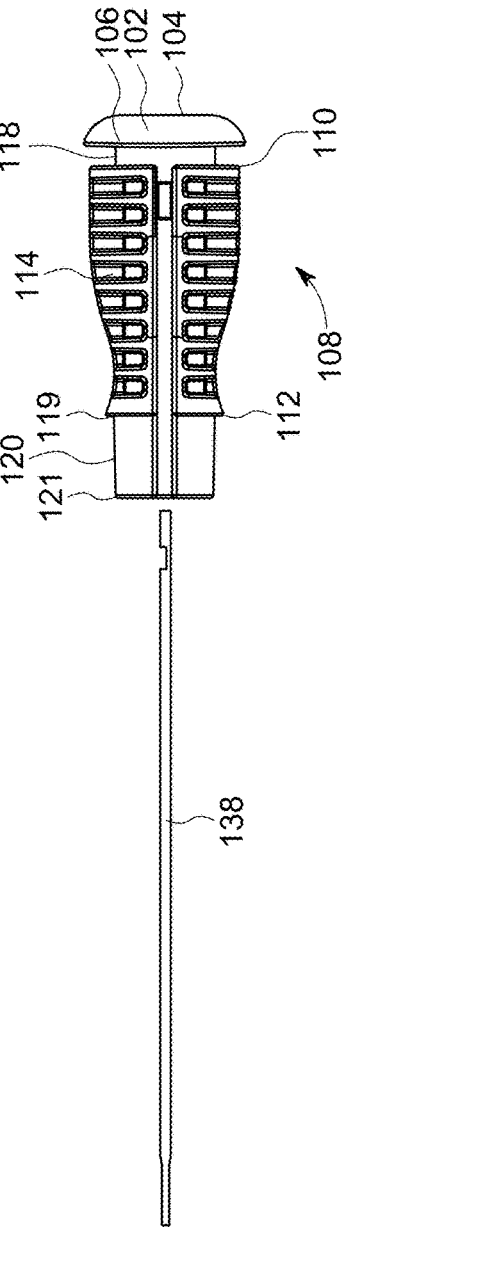
FIG. 12 is an exploded bottom view of an exemplary drill guide and inserter system for facilitating implantation of an implant system, in accordance with the present disclosure.
Figure 13:
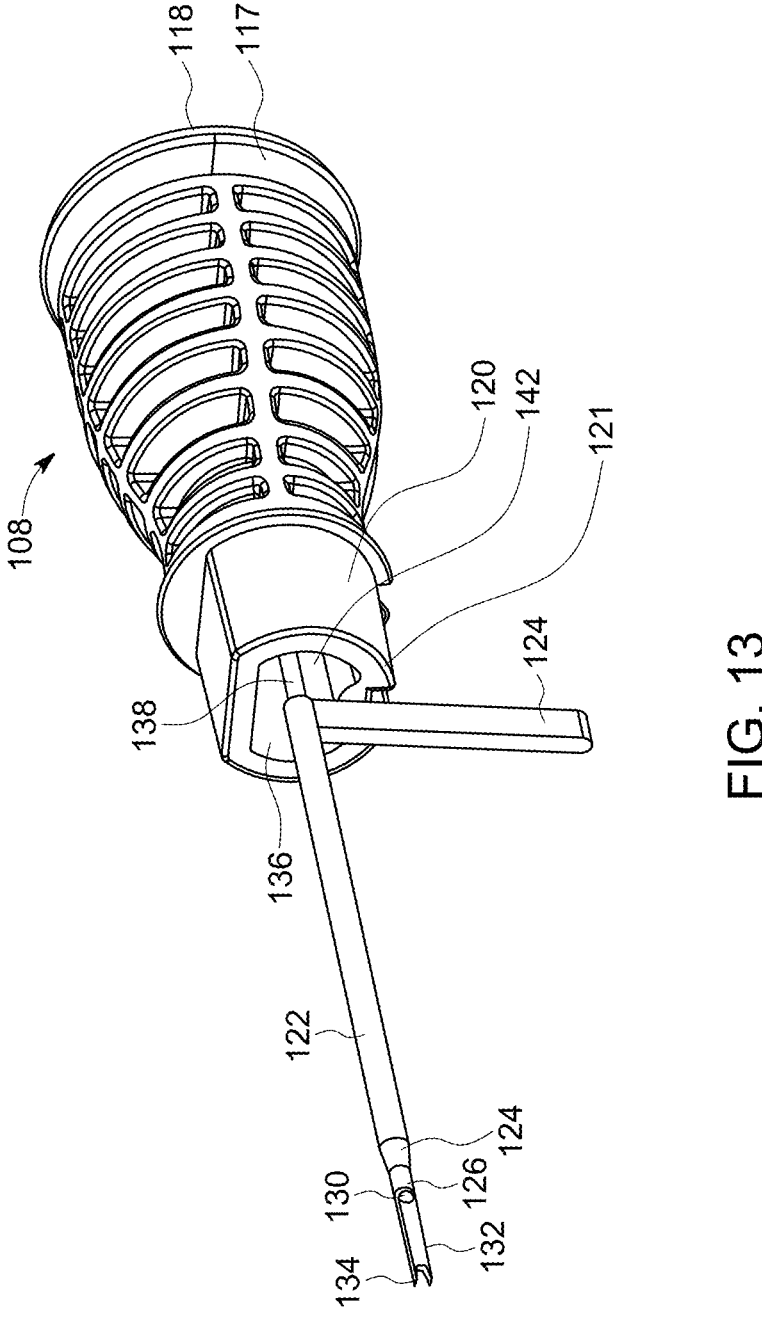
FIG. 13 is a front elevational, perspective view of an exemplary drill guide and inserter system for facilitating implantation of an implant system, in accordance with the present disclosure.
Figure 14:
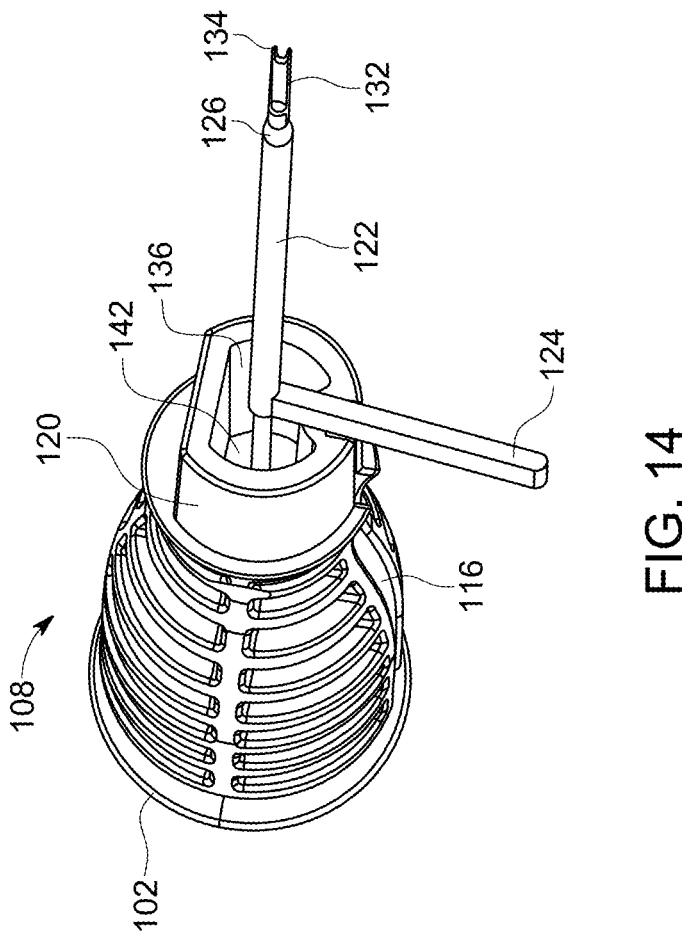
FIG. 14 is a front elevational, perspective view of an exemplary drill guide and inserter system for facilitating implantation of an implant system, in accordance with the present disclosure.

The handle portion 108 may include an inserter aperture, groove or cavity 116 (see FIG. 4) extending from the proximal end 110 of the handle portion 108 to the distal end 112 the handle portion 108 and toward the inserter portion 138 and the guide portion 122 and may be configured to accept therein or mate with a first coupling portion or groove 118 at the proximal end 110 of the handle portion 108 and a second coupling portion 120 at the distal end 112 of the handle portion 108 as shown in FIGS. 4 and 14, for example. The cavity 116 may be open or exposed at the distal end 112 of the handle portion 108 and may be open or exposed at the proximal end 110 of the handle portion 108. The cavity 116 may further be open or exposed at the distal end 121 of the second coupling portion 120 of handle portion 108 and may be open or exposed at the proximal end 119 of the second coupling portion, 120 of handle portion 108 thereby forming a slot or opening 136 (see FIGS. 13 and 14) at the distal end 121 of the second coupling portion 120.

As shown in FIGS. 5 and 13-15, the inserter portion 138 and the handle portion 108 are cannulated, hollow or otherwise include cooperating through holes that form an internal passageway or through hole 140 that may extend through the inserter portion 138 from the tip portion 134 of the inserter portion 138 and the tip portion of the insertion portion 132 to the proximal end 110 of the handle portion 108. The internal passageway 140 may also be open or exposed at the tip portion 134 of the inserter portion 138 and the tip portion of the insertion portion 132 and is also open or exposed at the proximal end 110 of the handle portion 108. The internal passageway 142 through the handle portion 108 may extend for the length of the handle portion 108 and may extend for the length of the first coupling portion 118 of the handle portion 108 and the second coupling portion 120 of the handle portion 108. The inserter portion 138 may be surrounded by guide portion 122 to aid in deployment of an anchor during implant surgery.

The internal passageway 140 is configured to accept a corresponding drilling member (such as a k-wire, drill bit, or other elongate drilling mechanism) therethrough. With the tip portion 134 of the insertion portion 132 engaged with a bone, the inserter portion 138 may be introduced into the internal passageway 140 at the proximal end 110 of the handle portion 108, and advanced through internal passageway 140 of the handle portion 108 and the inserter portion 138 to the bone, all while the inserter portion 138 is proximate to a guide portion 122. The drilling member can then be rotated or otherwise utilized to create a hole or aperture into, and potentially through, the bone. At least a portion of the internal passageway 140 of the inserter portion 138 may approximate the cross-sectional size (e.g., diameter) of the drilling member to guide the drilling member and prevent the drilling member from wandering and/or angling during a drilling operation.

The inserter portion 138, the handle portion 108, and the guide portion 122 may include one or more holes, slots, or openings that extend through the exterior surfaces thereof to the internal passageway 140. The inserter portion 138, the handle portion 108, and the guide portion 122 may also include holes that extend from the tip portion 134 of the insertion portion 132 of inserter portion 138 to the proximal end 110 of the handle portion 108. The one or more holes may be in communication with the exterior of the drill guide and inserter system 100 (e.g., the exterior of the handle portion 108 and/or the exterior of the guide portion 122) and the internal passageway 140 and the internal passageway 142 to provide access to and from the internal passageway 140 and the internal passageway 142. The width of the hole is less than the cross-sectional size of the drilling member to prevent the drilling member from disengaging from the internal passageway 140 and the internal passageway 142 during a drilling operation. In one embodiment, the width of the hole may be greater than a cross-sectional size of the strands of a tensioning suture and the strands of a shuttle suture of an implant coupled or loaded onto the inserter portion 138.

As shown in FIGS. 1-4 and 7-12, one end of the inserter portion 138 is attached to the manually engageable handle portion 108 and the opposing end of the inserter portion 138 is attached to an insertion portion 132 that extends from or past a distal end 112 of the handle portion 108 and defines an implant holder free end or tip portion 134. The insertion portion 132, tip portion 134, and bone engagement free end of inserter 130 may extend beyond the guide portion 122. As noted above, the distal end 112 of the handle portion 108 may include a second coupling portion 120. The second coupling portion 120 has a distal end 121 that is adjacent to the inserter portion 138 and also has a proximal end 119 that is adjacent to the distal end 112 of the handle portion 108. The second coupling portion 120 is configured to extend into and securely mate with the cavity 116 extending from the proximal end 110 of the handle portion 108 to the distal end 112 of the handle portion 108 of the drill guide and the inserter system 100. The handle portion 108 may also include a stop surface proximate to the second coupling portion 120 of the handle portion 108 that is configured to abut against the distal end 110 of the handle portion 108 of the drill guide and inserter system 100 when the second coupling portion 120 of handle portion 108 is fully seated within the cavity 116. The handle portion 108 may also include a stop surface proximate to the first coupling portion 118 of the handle portion 108 that is configured to abut against the proximate end 110 of the handle portion 108 of the drill guide and inserter system 100 when the first coupling portion 118 of the handle portion 108 is fully seated within the cavity 116.

The handle portion 108 of the drill guide and inserter system 100 may include the internal cavity or passageway 142 that is in communication with the passageway 140 of the inserter portion 138 when the inserter portion 138 is fully mated with the handle portion 108. The handle portion 108 may include one or more of a slot, hole, or opening 114 that extends from the exterior surface the handle portion 108 to the internal passageway 142. The inserter portion 138 may include an internal passageway 140 which may extend from the tip portion 134 of the insertion portion 132 of the inserter portion 138 to the proximal end 110 of the handle portion 108, or may extend from the tip portion 134 of the insertion portion 132 of the inserter portion 138 to the proximal end 119 of the second coupling portion 120 of the handle portion 108. The internal passageway 140 may be in communication with the exterior of the handle portion 108 and the internal passageway 140. The slot 114 may also provide access to and from the internal passageway 140.

The proximal end 110 of the handle portion 108 may define an end surface that can be utilized to apply pressure to the inserter portion 138. In some embodiments, the proximal end 110 of the handle portion 108 may be defined by a removable end cap portion 102 that closes off and/or mates within the internal passageway 142 of the handle portion 108. The end cap portion 102 may include a distal end 106 of the end cap portion which may be adjacent to the first coupling portion 118 of the handle portion 108. The first coupling portion 118 of the handle portion 108 is further adjacent to the proximal end 110 of the handle portion 108. The end cap portion 102 may further include a proximal end 104 of the end cap portion 102. The end cap portion 102 may be a solid opaque end cap, a solid transparent end cap, and/or it may optionally include one or more holes.

The insertion portion 132 comprises a stiff elongate post or like member or portion. The insertion portion 132 is configured to extend through the entirety of the passageway 140 of the inserter portion 138 from the proximal end 110 of the handle portion 108 or from the proximal end 104 of the end cap portion 102 through the tip portion 134 (i.e., it may extend through the entirety of the passageway 142 of the handle portion 108 and the entirety of the passageway 140 of the inserter portion 138) when the second coupling portion 120 of the handle portion 108 is fully seated within the internal passageway 140 through the inserter portion 138, as shown in FIGS. 1-4, 7, and 8.

Also, as shown in FIGS. 1-4 and 7-12, the guide portion or component 122 may be configured to envelope or surround the inserter portion 138 and nest or otherwise couple together with the handle portion 108, via the second coupling portion 120 in the drill guide and inserter system 100. The guide portion 122 is proximate to a distal end to the medial end component 126, and the medial end component 126 is further proximate to the distal end to the distal end component 128. The medial end component 126 is thereby intermediate the guide portion 122 and the distal end component 128. The guide portion 122, the medial end component 126, and the distal end component 128 may, in one embodiment, surround the inserter portion 138 and attach to the distal end 121 of the second coupling portion 120 of the handle portion 108. The guide portion 122 may further include a feature to hold the guide portion static during deployment. For example, the guide portion 122 may include a guide handle 124 which may be useful to aid in deployment of an anchor. The guide portion 122 may be inserted into a bone hole prepared for insertion of an implant and may, therefore, be comprised of any material suitable for performing such function. Examples of materials may include, but are not limited to, a polymer, a plastic, and/or a metal. In one embodiment, the guide portion 122 is comprised of a thin-walled and optionally a flexible material. The guide portion 122 may be slotted and contain holes across the surface of the guide portion 122.

Figure 16:
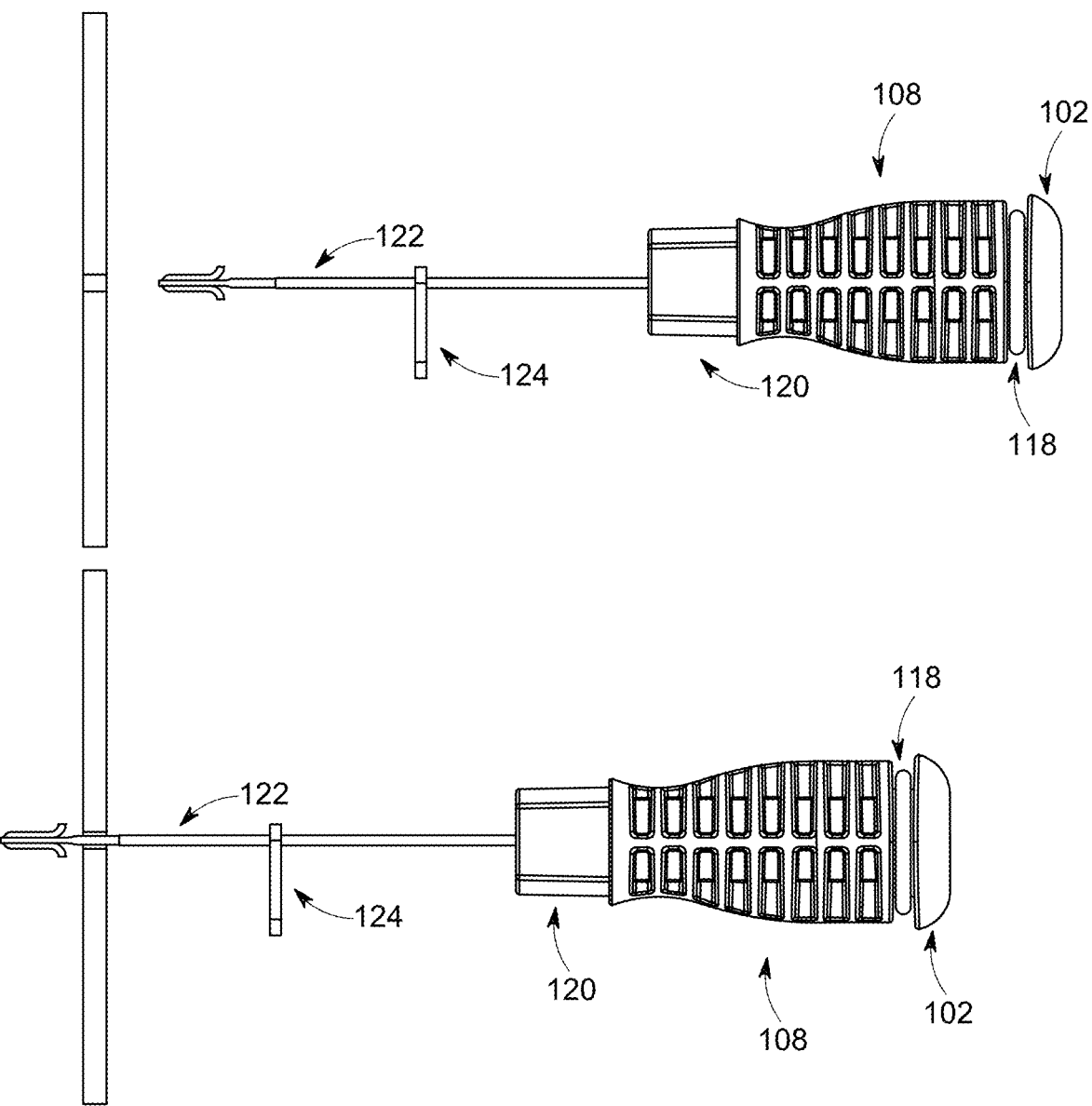
FIG. 16 illustrates an exemplary method of inserting an anchor through a bone hole via the drill guide and inserter system for facilitating implantation of an implant system, in accordance with the present disclosure.
Figure 17:
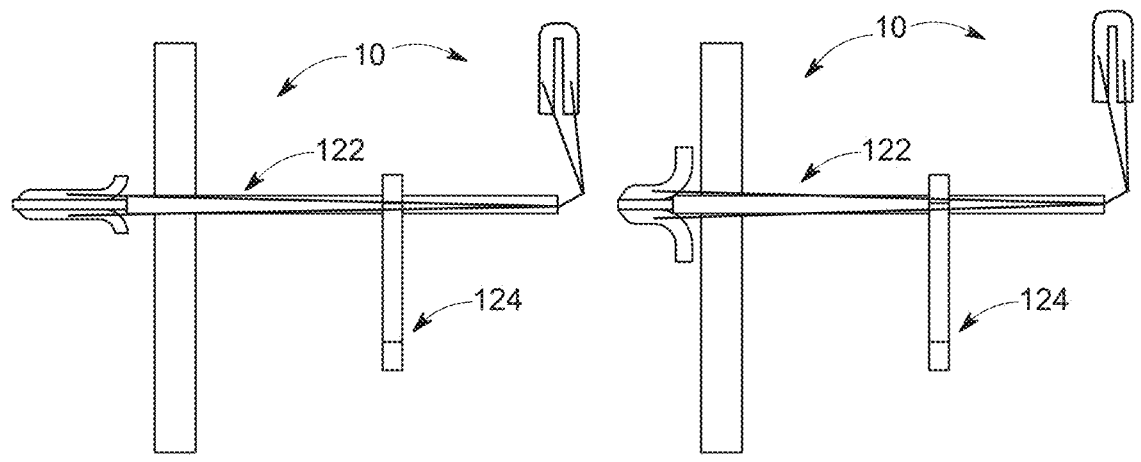
FIG. 17 illustrates an anchor deployment upon retraction of the insertion fork via the drill guide and inserter system for facilitating implantation of an implant system, in accordance with the present disclosure.

As shown in FIGS. 16 and 17, the guide portion 122 may be inserted behind an anchor of an implant and may further be kept in place while the inserter portion 138 and insertion portion 132 are removed during implant application. An anchor may deploy against the guide portion 122 rather than needing to rely on the cortical wall of the bone for such deployment and obviate the need to depend solely on the native bone quality and consistency for anchor deployment during implantation. The guide portion 122 may be a separate accessory instrument (as shown, for example, in FIGS. 16 and 17) or the guide portion 122 may be a removable or non-removeable feature of the inserter portion 138. The guide portion 122 may be in the form of a sleeve, in one embodiment, or, alternatively, may take the form other than a sleeve, such as a blunt obturator, a threaded slotted screw, and/or a cannulated screw/button, or any combination thereof. A suture coming from the anchor may go inside of the internal passageway 140 of the inserter portion 138 or, in an alternative embodiment, a suture may go on the outside of the inserter portion 138.

The implant holder tip portion 134 of the insertion portion 132 is configured to hold or retain an anchor of an implant, such as a tension anchor and/or a shuttle anchor of a bone and/or tissue joining implant system 10, as shown in FIG. 17. An anchor of an implant system 10 may thereby be pre-loaded on the tip portion 134, and one or more other portion of an implant may be coupled to or provided in/on the insertion portion 132. For example, a tension anchor and/or a shuttle anchor of the bone and/or tissue joining implant system 10 may be retained on the tip portion 134 of the inserter portion 138, and a tensioning suture and/or a shuttle suture may be provided/extend through the passageway 142 within the handle portion 108. A tension anchor or the shuttle anchor that is not retained on the tip portion 134 and/or a needle of an implant may be housed within the passageway 140 of the inserter portion 138 or coupled to the exterior of the inserter portion 138, for example. A tensioning suture and/or the shuttle suture, and/or a needle, may be removably coupled to a clip, post or another portion or mechanism of the inserter portion 138 such that a tensioning suture and/or a shuttle suture may apply tension to the tension anchor or the shuttle anchor that is on the tip portion 134 to releasably retain the tension anchor/shuttle anchor on the tip portion 134. The drill guide and inserter system 100 may be pre-loaded with an implant system.

When the inserter portion 138 is fully mated with the handle portion 108, the drill guide and inserter system 100 is configured such that a tension anchor and/or a shuttle anchor of an implant that is retained on the tip portion 134 is positioned past the tip portion 134 of the inserter portion 138, and any tensioning sutures and/or the shuttle sutures extend through the passageway 140 of the inserter portion 138 and the passageway 142 of the handle portion 108. However, tensioning sutures and shuttle sutures may be removed from the passageway 140 of the inserter portion 138 and the passageway 142 of the handle portion 108 by passing a tensioning suture and/or a shuttle suture through the hole 114 of the handle portion 108 and the slot of opening 136 on the distal end of the second coupling portion 120 of the handle portion 108.

Figure 15:
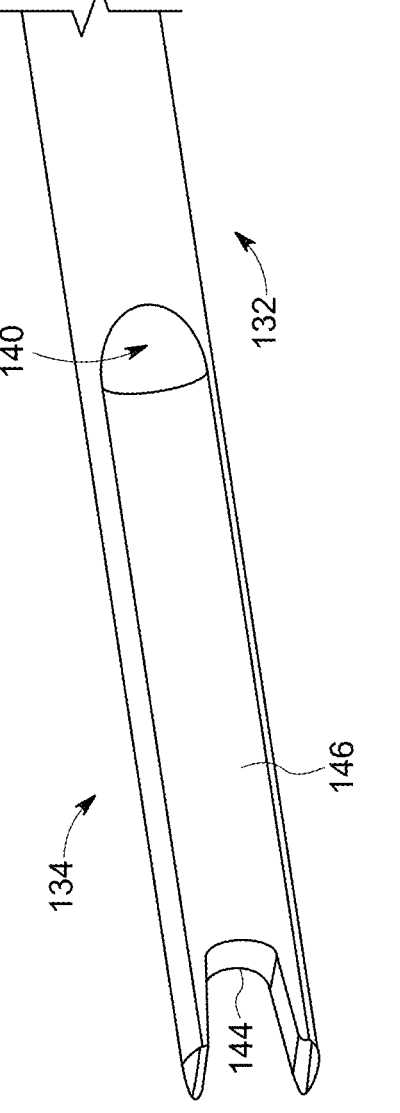
FIG. 15 is a perspective view of an implant retaining tip of the inserter of the drill guide and inserter system for facilitating implantation of an implant system of FIG. 1, in accordance with the present disclosure.

As shown in FIG. 15, the implant holder tip portion 134 of the insertion portion 132 of the inserter portion 138 may include a forked free end 144 and a pair of grooves 146 extending proximally from the base of the forked free end 144 along differing (e.g., opposing) sides of the insertion portion 132. The forked free end 144 and at least one groove 146 are configured to retain or mate with an anchor of an implant system (e.g., a tension anchor or a shuttle anchor of an implant system) with a medial portion of an anchor extending over the base of the forked free end 144 between the tines or arms thereof and end portions of an anchor extending within and along the grooves 146. The implant holder tip portion 134 may be configured such that the implant holder tip portion 134 is stiff, and thereby utilized to insert or pass an anchor retained thereon into and through a hole in at least soft tissue and/or a bone.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A bone and/or tissue joining system, comprising:
   an instrument system for implanting a bone and/or tissue joining implant system, comprising:
   a handle portion;
   an inserter portion comprising an insertion portion extending from a distal handle end portion of the handle portion to a tip portion that defines a free end of the inserter portion; and
   a guide portion comprising a proximal end portion, a distal end portion and a passageway extending through the guide portion between the medial and distal end portions,
   wherein the guide portion and the inserter portion are mated such that the inserter portion extends through the passageway of the guide portion and the guide portion is freely slidably received on the inserter portion,
   wherein the guide portion and inserter portion are configured such that in a pre-implant arrangement thereof, the tip portion of the inserter portion is positioned past the distal end portion of the guide portion,
   wherein the tip portion comprises a pair of grooves extending proximally from a forked free end,
   wherein the distal end portion of the guide portion comprises a distal engagement portion that is narrower than a proximal portion of the distal end portion of the guide portion, wherein the distal engagement portion of the distal end portion of the guide portion extends about and engages an exterior surface of the inserter portion, and the proximal portion of the distal end portion is spaced from the exterior surface of the inserter portion.

2. The system according to claim 1, wherein the forked free end comprises a pair of tines and a base portion extending therebetween.

3. The system according to claim 2, wherein the pair of grooves extend proximally from portions of the base portion between the pair of tines.

4. The system according to claim 1, wherein the pair of grooves are positioned on substantially opposing sides of the insertion portion.

5. The system according to claim 1, wherein at least one tine of the pair of tines forms a bone engaging tooth with a pointed tip.

6. The system according to claim 1, wherein the guide portion further comprises a guide handle extending laterally from the insertion portion.

7. The system according to claim 1, wherein the guide portion and inserter portion are configured such that in the pre-implant arrangement thereof, the proximal end portion of the guide portion is positioned distally of the distal handle end portion of the handle portion.

8. The system according to claim 1, wherein the guide portion and the inserter portion are mated such that the guide portion is freely slidable off the inserter portion by translating distally over the tip portion.

9. The system according to claim 1, further comprising the bone and/or tissue joining implant system, the bone and/or tissue joining implant system comprising a first soft bone anchor mounted on the forked free end.

10. The system according to claim 9, wherein the first soft bone anchor extends over the forked free end and along the pair of grooves.

11. The system according to claim 9, wherein the bone and/or tissue joining implant system further comprises at least one suture member extending through the first soft bone anchor in a configuration that deforms the first soft bone anchor.

12. The system according to claim 11, wherein the handle portion comprises a first groove that extends along a length of handle portion and is in communication with a second groove that extends about a portion of the handle portion.

13. The system according to claim 12, wherein the first soft bone anchor extends over the forked free end and along the pair of grooves.

14. The system according to claim 13, wherein the forked free end comprises a pair of tines and a base portion extending therebetween, and wherein a medial portion of the first soft bone anchor extends over the base portion and end portions of the first soft bone anchor extend along the pair of grooves.

15. The system according to claim 11, wherein the bone and/or tissue joining implant system further comprises a second soft bone anchor, and wherein the at least one suture member extends through the second soft bone anchor in a configuration that deforms the second soft bone anchor via tensioning of the at least one suture member.

16. A method of forming a bone and/or tissue joining implant system, the method comprising:
   obtaining an instrument system for implanting a bone and/or tissue joining implant system, the instrument system comprising:
   a handle portion;

an inserter portion comprising an insertion portion extending from a distal handle end portion of the handle portion to a tip portion that defines a free end of the inserter portion; and a guide portion comprising a proximal end portion, a distal end portion and a passageway extending through the guide portion between the medial and distal end portions, wherein the guide portion and the inserter portion are mated such that the inserter portion extends through the passageway of the guide portion and the guide portion is freely slidably received on the inserter portion, wherein the guide portion and inserter portion are configured such that in a pre-implant arrangement thereof, the tip portion of the inserter portion is positioned past the distal end portion of the guide portion, wherein the tip portion comprises a pair of grooves extending proximally from a forked free end, and wherein the distal end portion of the guide portion comprises a distal engagement portion that is narrower than a proximal portion of the distal end portion of the guide portion, wherein the distal engagement portion of the distal end portion of the guide portion extends about and engages an exterior surface of the inserter portion, and the proximal portion of the distal end portion is spaced from the exterior surface of the inserter portion; and mounting a first soft bone anchor of the bone and/or tissue joining implant system on the forked free end, the bone and/or tissue joining implant system further comprising at least one suture member extending through the first soft bone anchor in a configuration that deforms the first soft bone anchor via tensioning of the at least one suture member.

17. A bone and/or tissue joining system, comprising:

an instrument system for implanting a bone and/or tissue joining implant system, comprising:

a handle portion;

an inserter portion comprising an insertion portion extending from a distal handle end portion of the handle portion to a tip portion that defines a free end of the inserter portion; and a guide portion comprising a proximal end portion, a distal end portion and a passageway extending through the guide portion between the medial and distal end portions, wherein the guide portion and the inserter portion are mated such that the inserter portion extends through the passageway of the guide portion and the guide portion is freely slidably received on the inserter portion, wherein the guide portion and inserter portion are configured such that in a pre-implant arrangement thereof, the tip portion of the inserter portion is positioned past the distal end portion of the guide portion, wherein the tip portion comprises a pair of grooves extending proximally from a forked free end, wherein the inserter portion comprises a second passageway through the insertion portion from the distal handle end portion of the handle portion to the tip portion, and wherein the guide portion extends from a distal end portion of the handle portion to the tip portion of the inserter portion.

18. The system according to claim 17, wherein the distal end portion of the guide portion comprises a distal engagement portion that is narrower than a proximal portion thereof.

19. The system according to claim 18, wherein the distal engagement portion extends about and engages an exterior surface of the inserter portion, and the proximal portion of the distal end portion of the guide portion is spaced from the exterior surface of the inserter portion.

20. The system according to claim 17, wherein the handle portion comprises a hole that extends from an exterior surface of the handle portion to the second passageway.

* * * * *